United States Patent [19]

Bodor et al.

[11] 4,154,824

[45] May 15, 1979

[54] NONBITTER TASTING POTASSIUM PRODUCT FOR ORAL ADMINISTRATION TO WARM-BLOODED ANIMALS AND METHOD FOR PREPARING SAME

[75] Inventors: Nicolae S. Bodor; Takeru Higuchi, both of Lawrence, Kans.

[73] Assignee: INTERx Research Corporation, Lawrence, Kans.

[21] Appl. No.: 707,008

[22] Filed: Jul. 20, 1976

[51] Int. Cl.$^2$ .............................................. A61K 31/66
[52] U.S. Cl. ..................................................... 424/205
[58] Field of Search ...................... 424/94, 48, 56, 180, 424/205, 153

[56] References Cited

U.S. PATENT DOCUMENTS

| | | | |
|---|---|---|---|
| 2,170,274 | 8/1939 | Morgan | 260/987 |
| 2,691,035 | 10/1954 | Thomas | 260/987 |
| 2,834,678 | 5/1958 | Hanson | 424/94 |
| 3,356,570 | 8/1967 | Polli et al. | 424/153 |

OTHER PUBLICATIONS

Chem. Abst. - 2407d, (1966).

*Primary Examiner*—Stanley J. Friedman
*Attorney, Agent, or Firm*—Bacon & Thomas

[57] ABSTRACT

Potassium is rendered nonbitter tasting by combining the same with phytic acid. The final product is useful as a nonbitter tasting potassium supplement for warm-blooded animals deficient in levels of potassium.

9 Claims, No Drawings

NONBITTER TASTING POTASSIUM PRODUCT FOR ORAL ADMINISTRATION TO WARM-BLOODED ANIMALS AND METHOD FOR PREPARING SAME

BACKGROUND OF THE INVENTION

1. FIELD OF THE INVENTION

The present invention relates to a means for delivering nonbitter tasting potassium orally to warm-blooded animals. More particularly, the present invention concerns achievement of the above goal with the potassium salts of phytic acid.

2. DESCRIPTION OF THE PRIOR ART

By way of background, potassium is administered to patients normally suffering from congestive heart failure or patients maintained on diuretics. Conventionally, potassium is administered via a pharmaceutically acceptable salt thereof, i.e. potassium chloride, either in tablet or liquid dosage form. The former dosage form, though still prescribed, is highly undesirable as recent studies reveal that administering potassium in this manner can often cause ulceration of the gastrointestinal tract. In the latter dosage form, which is the most widely employed, patient acceptance is minimal, if any, due to the highly undesirable aftertaste of potassium. While numerous attempts have been made to mask the taste of potassium chloride, either via formulation or by chemical modification, the results of such attempts have met with little, if any, success.

Accordingly, it is quite obvious that a need exists for a nonbitter tasting potassium product which can be orally administered and yet be substantially free of any unwanted bitter metallic aftertaste as is associated with the prior art liquid formulated products.

In the past, alkali and alkaline earth metal salts of phytic acid have been, among other things, used as a source of phytic acid, fire retardants, plasticizers, antiscum agents and antifoam agents. Their use as a therapeutic source of potassium and the recognition of their nonbitter taste has not been shown by the prior art. See, U.S. Pat. Nos. 2,493,666, 2,497,602, 2,497,603 2,718,523 and 3,591,665.

Additionally, the natural product "phytin" (which is employed as a source of calcium, magnesium and phosphorous) contains trace amounts of potassium; however, this is negligible from a therapeutic standpoint. Moreover, phytin is practically insoluble and thus is virtually nonbioavailable when orally administered. See, U.S. Pat. No. 2,834,678.

SUMMARY OF THE INVENTION

The foregoing object is met by administering to warm-blooded animals in need of potassium supplementation, and particularly, mammalians, a potassium salt of phytic acid having the following formula:

$$C_6H_6[(OPO)_6(OH)_x(OK)_y]$$

wherein x and y each represent an integer of from 0 to 12, with the proviso that the sum of x and y must always equal 12.

DETAILED DESCRIPTION OF THE INVENTION

The above-identified salts can be prepared in a number of ways, one of which is by reacting, at standard temperature and pressure, commercially available or prepared "in situ" phytic acid with the desired stoichiometric amount of potassium hydroxide, depending on which stoichiometric salt one desires to obtain. That is, depending upon the stoichiometric amount of potassium hydroxide employed, one can obtain the mono- through dodecyl- potassium salts of phytic acid. If necessary, the commercially available phytic acid employed can be purified via passing the same through charcoal, the charcoal being present in an amount of at least four percent (4%) by weight of the phytic acid employed. Once the reaction is complete, the final product is then isolated by any conventional method such as evaporation, filtration or lypholization. Lypholization is conducted in accordance with standard lypholization procedures over a period of from two to five days, thus yielding the final product, i.e., the mono- through dodecyl- potassium phytate salt. Additional methods for preparing these salts are noted in U.S. Pat. Nos. 2,493,666, 2,497,602, 2,497,603, 2,718,523 and 3,270,064.

While all the potassium salts of phytic acid suffice for applicants' purposes, nevertheless, the hexa- (6K), nonyl- (9K) and docecyl- (12K) salts are preferred.

The potassium phytate salts of the present invention are administered orally to warm-blooded animals in any conventional solid chewable or liquid dosage form such as a chewable tablet, aqueous solution, aqueous-alcoholic elixirs, syrups, etc. While any skilled artisan can readily recognize these dosage forms available, such forms can be chosen from among those noted in "REMINGTON'S PHARMACEUTICAL SCIENCES," Fourteenth Edition (1970), Mack Publishing Company, as well as the current edition of the text entitled "PHYSICIANS' DESK REFERENCE," under the heading "potassium." Naturally, these salts can also be formulated in conventional tablet, gelatin capsule, "soft" gelatin capsule or any other orally and equivalent acceptable form as well.

The dose administered, whether a single dose or a daily dose, will, of course, vary because of the needs and size of the individual patient receiving the same. The dosage administered is not subject to definite bounds, but it will usually be an effective amount or the equivalent on a molar basis of the pharmacologically active form produced (elemental potassium) upon the metabolic release of the potassium to achieve its desired pharmacological and physiological effect, i.e., potassium supplementation. Stated another way, the dose for the potassium phytate salts of this invention will mimic the dosage regimen for liquid potassium supplements already available on the market today.

In order to further enhance dissolution and/or bioavailability, the potassium phytate salts of this invention can be administered as a "mixed" salt, whereby some of the potassium ions can be replaced by sodium, calcium or magnesium ions or a combination thereof. Generally, when a "mixed" salt is desired, the ratio or percent of potassium ions to sodium, calcium or magnesium ions will be at least 50—50 to ensure potassium bioavailability.

Without further elaboration, it is believed that one of ordinary skill in the art can, using the preceding description, utilize the present invention to its fullest extent. Consequently, the following specific embodiments are, therefore, to be construed as merely illustrative, and not limitative, of the remainder of the specification and claims in any way whatsoever.

EXAMPLE I

By following the procedure described earlier and using stoichiometric amounts of potassium hydroxide, each of the hexa-, nonyl- and dodecyl- potassium salts of phytic acid were prepared.

On day one (1), human volunteers of both sexes were asked to sample taste potassium chloride, a conventional potassium supplement. Each individual so sampling physically exhibited and verbally attested to the bitter and metallic aftertaste of the compound.

On days two (2), three (3) and four (4), the same human volunteers sample tasted, respectively, each of the hexa-, nonyl- and dodecyl- potassium phytate salts of the present invention. No physical signs of distaste with the salts sampled were observed. All volunteers verbally expressed and confirmed the nonbitter taste of each salt sampled.

Substantially similar results are observed when the remaining potassium phytate salts of the present application are orally administered.

From the foregoing description, one of ordinary skill in the art can easily ascertain the essential characteristics of this invention, and without departing from the spirit and scope thereof, can make various changes and/or modifications to the invention for adapting it to various usages and conditions. Accordingly, such changes and modifications are properly, equitably and intended to be, within the full range of equivalence of the following claims.

What we claim is:

1. A method for orally administering potassium to a warm-blooded animal in need of potassium supplementation without imparting a metallic potassium aftertaste which comprises administering thereto, a therapeutically effective amount of a potassium phytate salt having the formula:

$$C_6H_6[(OPO)_6(OH)_x(OK)_y]$$

wherein x and y represent an integer of from 0 to 12, with the proviso that the sum of x and y must always equal 12.

2. The method of claim 1, wherein said salt is hexapotassium phytate.
3. The method of claim 1, wherein said salt is nonylpotassium phytate.
4. The method of claim 1, wherein said salt is dodecylpotassium phytate.
5. The method of claim 1, wherein said warm-blooded animal is a mammal.
6. The method of claim 1, wherein said salt is maintained in combination with an orally and pharmaceutically acceptable solid chewable or liquid carrier.
7. The method of claim 1, wherein said potassium phytate salt is a mixed salt of potassium with a member selected from the group consisting of sodium, calcium, magnesium, or combinations thereof, said mixed salt comprising at least 50% potassium ions.
8. The method of claim 1, wherein said salt is administered in solid dosage form.
9. The method of claim 1, wherein said salt is administered in liquid dosage form.

* * * * *